United States Patent [19]
Hutter

[11] Patent Number: 5,934,803
[45] Date of Patent: Aug. 10, 1999

[54] APPARATUS AND METHOD FOR MIXING MULTI-PART REACTION MATERIALS UNDER VACUUM

[75] Inventor: Peter S. Hutter, Aspen, Colo.

[73] Assignee: Physical Systems, Inc., Aspen, Colo.

[21] Appl. No.: 08/961,454

[22] Filed: Oct. 30, 1997

[51] Int. Cl.[6] .................................................. B01P 13/06
[52] U.S. Cl. ...................................... 366/139; 366/326.1
[58] Field of Search ................................ 366/139, 326.1, 366/309, 312, 329.1, 329.3

[56] References Cited

U.S. PATENT DOCUMENTS

| | | |
|---|---|---|
| 3,144,966 | 8/1964 | Cook . |
| 4,015,945 | 4/1977 | Frankel et al. . |
| 4,185,072 | 1/1980 | Puderbaugh et al. ................... 366/248 |
| 4,758,096 | 7/1988 | Gunnarsson . |
| 4,808,184 | 2/1989 | Tepic . |
| 4,973,168 | 11/1990 | Chan ...................................... 366/139 |
| 5,004,501 | 4/1991 | Faccioli et al. . |
| 5,114,240 | 5/1992 | Kindt-Larsen et al. ................ 366/129 |
| 5,252,301 | 10/1993 | Nilson et al. ............................ 366/242 |
| 5,265,956 | 11/1993 | Nelson et al. ........................... 366/139 |
| 5,368,386 | 11/1994 | Murray ..................................... 366/139 |
| 5,370,221 | 12/1994 | Magnusson et al. .................... 206/221 |
| 5,398,483 | 3/1995 | Smith et al. ............................. 206/219 |
| 5,415,474 | 5/1995 | Nelson et al. ........................... 366/139 |
| 5,435,645 | 7/1995 | Faccioli et al. ......................... 366/139 |
| 5,443,182 | 8/1995 | Tanaka et al. . |
| 5,501,520 | 3/1996 | Lidgren et al. ......................... 366/139 |
| 5,588,745 | 12/1996 | Tanaka et al. . |

*Primary Examiner*—Tony G. Soohoo
*Attorney, Agent, or Firm*—Sheldon & Mak

[57] ABSTRACT

An apparatus for mixing multi-part reaction materials under a vacuum comprises a container including a mixing chamber sized to contain a reaction material. An agitator for mixing the reaction material to form a mix includes both rigid blades and flexible paddles. The rigid blades are substantially non-deflected during mixing and cut the mix, and the flexible paddles are deflected and knead the mix. The combined action of the rigid blades and the flexible paddles under vacuum throughly mixes reaction materials and removes entrapped gases from the mix. The mix can be dispensed directly from the mixing chamber. The apparatus can be used to mix viscous materials such as bone cement.

23 Claims, 3 Drawing Sheets

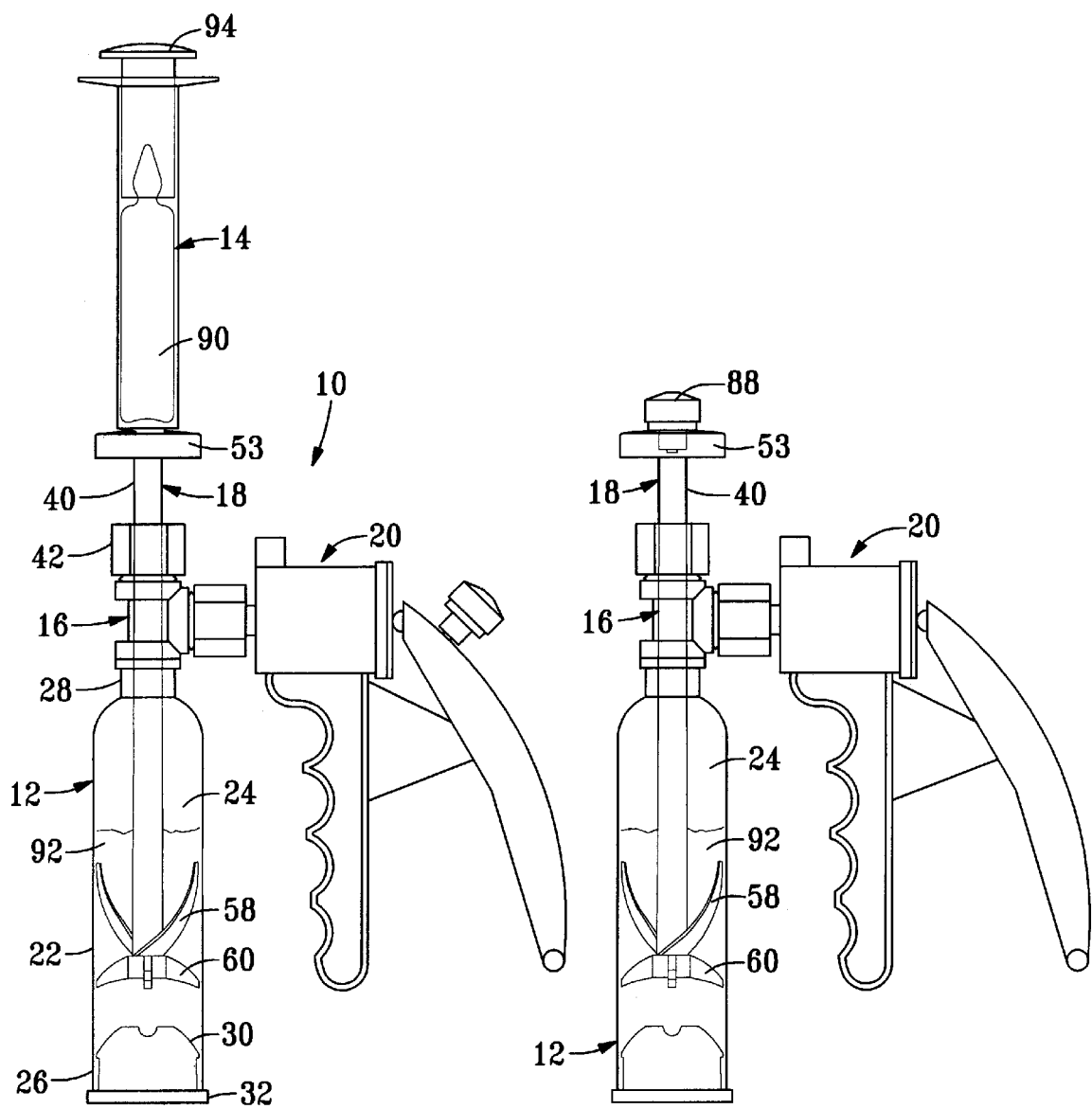

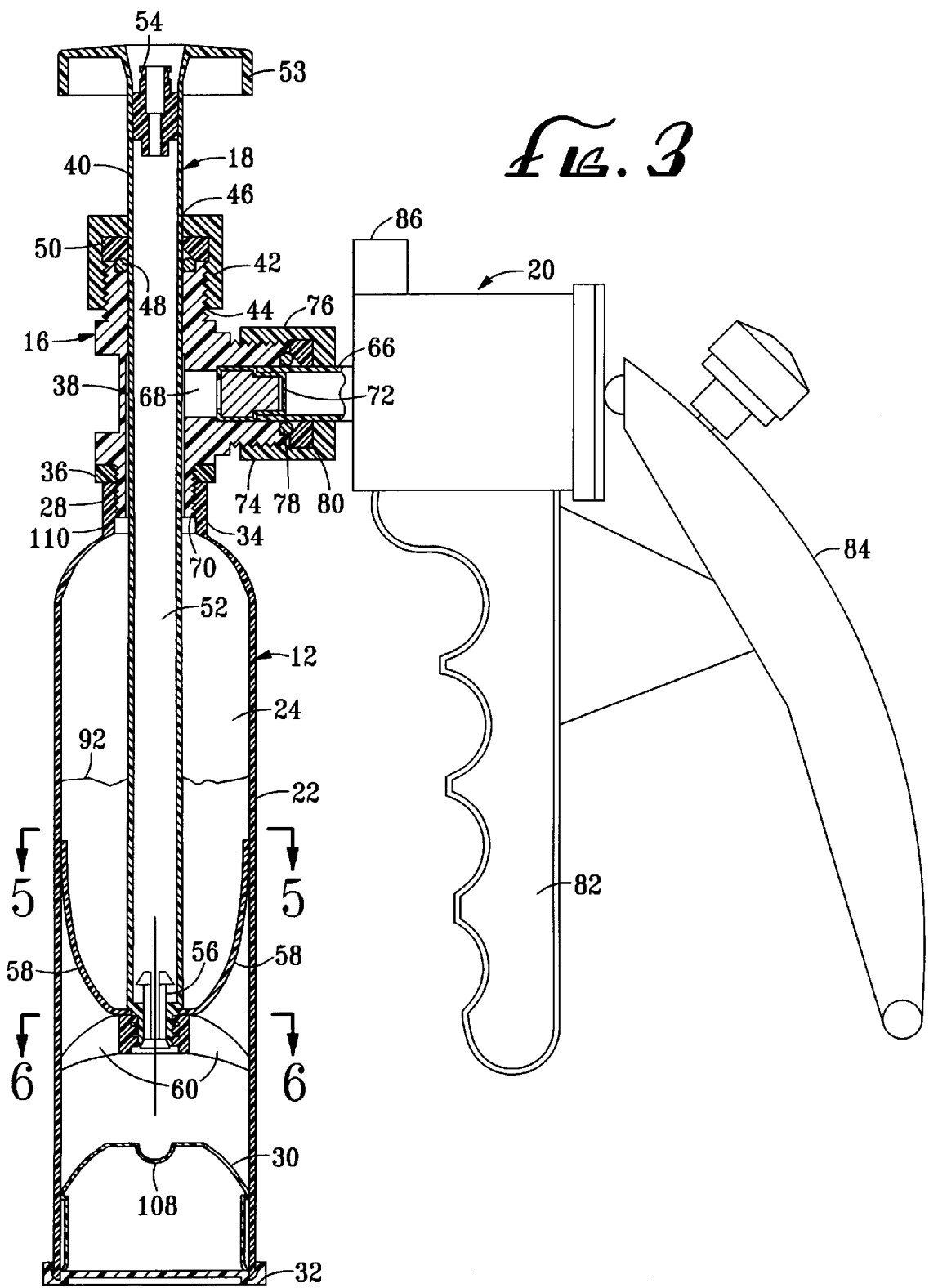

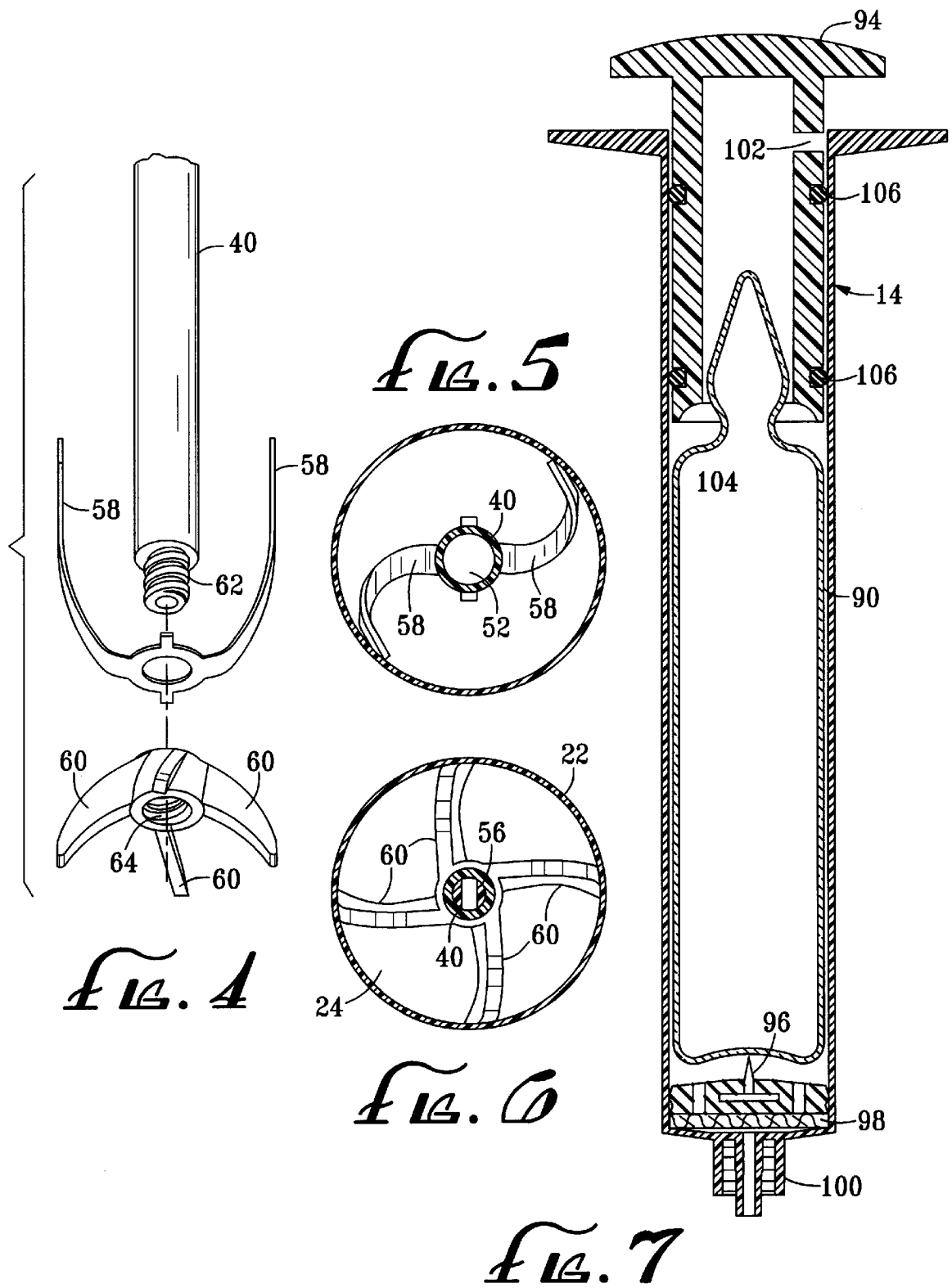

APPARATUS AND METHOD FOR MIXING MULTI-PART REACTION MATERIALS UNDER VACUUM

BACKGROUND

The present invention relates to an apparatus and method for mixing multi-part materials under vacuum and for dispensing the mix from the apparatus.

Multi-part reaction materials are commonly mixed under vacuum to eliminate entrapped air and gaseous reaction byproducts from the mix. The mixing vessel can be evacuated after mixing, but before use, or during mixing. Certain materials have relatively shorter set times and higher viscosity. It is more difficult to remove gases from these materials for several reasons. First, bubbles formed during mixing must migrate through the viscous mix to reach a surface exposed to vacuum. Second, the vacuum level that can be used during mixing is limited by the boiling points of the parts, as in bone cement; the differential pressure attainable at a given altitude; and the capabilities of the apparatus that creates the vacuum.

A known method for mixing bone cement to increase the rate of entrapped gas elimination comprises pre-evacuating the space surrounding one part of the cement prior to mixing, and then introducing the other part into the evacuated space. This method is less than completely satisfactory, however, because the turbulence caused by the second part filling the evacuated space can cause bubbles and voids to form in the mix.

It is also known to force a first part to replace the interstitial air in a second part. The air present in second material is displaced; but the method does not quickly and thoroughly mix the two materials, remove the gaseous reaction byproducts, or compensate for temperature.

It is important in the mixing of certain multi-part materials, that the materials be quickly combined and that the mix, de-air and de-gas steps be performed quickly, so as to protect the mix from outside contamination. Avoiding contamination is especially important in the mixing of bone cement under sterile surgical conditions. Generally, bone cements have a mix schedule, from the addition of a liquid monomer to a powder component, of one minute for mixing followed by one minute of pot life, before the mix needs to be injected. Accordingly, the efficiency of the mixing step is very important.

Some known methods of mixing bone cements comprise mixing materials within a container from which the mix is subsequently extruded, and applying a vacuum to the container during the mix, or both during and after the mix. Known methods agitate the bone cement mix to enhance mixing within the time constraints of the mixing process. Flat plate agitators having various hole patterns have been used to accomplish the mix. The mixed material can be extruded from the mixing chamber through the plate. Mixing only occurs when the agitator is moved in and out of the mixing chamber. Rotary motion repositions the holes for axial plunging, but provides only minimal mixing.

Another important consideration in regard to multi-part reaction materials is that the parts be readily accessible and easily handeable before and during the mixing procedure.

Bone cement liquid monomer is an example of a component of a multi-part reaction material that is difficult to handle. The monomer is usually delivered by the bone cement manufacturer in a glass vial, which is broken to add the monomer to the powder component. The monomer may not always be stored within the container in which the mixing is performed, and may be supplied separately from the device. This can make the mixing procedure more difficult to perform.

During the mixing of multi-part reaction materials under vacuum, gases can be evolved. These gases can be toxic to humans, and so it is important to prevent these gases from escaping into the environment.

Accordingly, there is a need for an apparatus for mixing and dispensing multi-part reaction materials that (i) can rapidly combine the materials to meet mix schedules, (ii) does not cause cavitation in the mix, reducing the entrapment of air and out-gassing; (iii) efficiently agitates the reaction materials throughout substantially the entire mixing chamber; (iv) can quickly establish and also maintain a vacuum in the mixing chamber; (v) exposes a large amount of surface area of the mix to vacuum during agitation, enabling trapped air and reaction gases to escape from even viscous mixes.

SUMMARY

The present invention provides an apparatus and method for mixing multi-part reactions materials under a vacuum that satisfies the above needs. The apparatus comprises a first container including a wall defining an open first end, an open second end and a mixing chamber. The mixing chamber is sized to contain the reaction material during mixing.

The reaction material typically comprises a first part and a second part. For bone cement, the first part is a powder material and the second part is a liquid.

A closure can be provided at the second end of the first container to form an airtight seal.

An agitator includes an agitator rod partially disposed in the mixing chamber and extending outwardly of the first container through the first end. The agitator rod preferably includes a bore through which the second part is introduced into the mixing chamber containing the first part.

The agitator comprises at least one rigid blade. The apparatus preferably comprises at least four rigid blades. The rigid blades are sufficiently rigid so that they maintain their shape and are not deflected during mixing of the reaction materials, such that the rigid blades can cut through the mix.

The agitator also comprises at least one flexible paddle fixedly attached to the agitator rod. The apparatus preferably comprises at least two flexible paddles. The flexible paddles are sufficiently flexible to be deflected during mixing of reaction materials, such that the flexible paddles knead the mix.

The flexible paddles and the rigid blades preferably contact the wall of the mixing chamber to remove any reaction material adhered on the wall during mixing.

A connector is typically attached to the first container at the second end. The connector can include a first passage through which the agitator rod extends, and a second passage through which gases are drawn from the mixing chamber to produce a vacuum.

The second part of the reaction material is typically stored in a second container that can be removably attached to the connector.

The apparatus can comprise a vacuum pump attachable to the connector. The vacuum pump draws gases from the mixing chamber and can also pull the second part into the mixing chamber. The first and second parts of the reaction material are mixed by the agitator.

The apparatus can also comprise a vacuum indicator to indicate the vacuum pressure in the mixing chamber.

The apparatus can comprise a plunger sized to be inserted into the mixing chamber. The plunger moves axially in the mixing chamber during dispensing of the mix from the first container.

The apparatus is particularly suitable for mixing multi-part reaction materials such as bone cement, including a liquid part and a solid part. The solid part is typically a powder that can be stored in the mixing chamber and the liquid part can be stored in the second container. The apparatus protects the components from the environment prior to the mixing. The two parts can be added to each other typically in accordance with manufacturer specifications.

The present invention provides important advantages that enable rapid, uniform mixing of multi-part reaction materials under vacuum, including (i) rapid introduction of one part into another part, without causing cavitation in the mix and also reducing the entrapment of air; (ii) agitation of the mix throughout a substantial portion of the mixing chamber; (iii) agitation that exposes a large amount of surface area of the mix to vacuum, to enhance the escape of gases from the mix; (iv) an agitator that cuts the mix and scrapes the mixing chamber wall to plow one part into the other, without causing cavitation and out-gassing, and that also kneads the mix; and (v) the ability to quickly establish a vacuum in the mixing chamber and to maintain the vacuum.

DRAWINGS

These and other features, aspects and advantages of the present invention will become better understood from the following description, appended claims and accompanying drawings, where:

FIG. 1 is a side elevational view of an apparatus for mixing multi-part materials under vacuum according to the present invention, prior to the introduction of one part of a reaction material into a mixing chamber containing another part of the reaction material;

FIG. 2 illustrates the apparatus of FIG. 1 after the two parts are combined in the mixing chamber;

FIG. 3 is a partial cross-sectional view of the apparatus of FIG. 2;

FIG. 4 is an illustrational view showing the manner of attachment of the rigid blades and flexible paddles to an agitator rod of the apparatus;

FIG. 5 is a cross-sectional view in the direction of line 5—5 of FIG. 3 showing the configuration of the flexible paddles;

FIG. 6 is a cross-sectional view in the direction of line 6—6 of FIG. 3 showing the configuration of the rigid blades; and FIG. 7 is a cross-sectional view showing a breakable container for storing one of the parts of the reaction material.

DESCRIPTION

With reference to the drawings, an apparatus 10 for mixing and dispensing multi-part reaction materials comprises a first container 12 for containing a first component or first part of a reaction material. The apparatus can also comprise a second container 14 for containing a second component or a second part of the reaction material and a connector 16 attached to the first container 12. An agitator 18 is provided to mix the reaction material. The apparatus 10 can comprise a vacuum means such as a vacuum pump 20 to form a vacuum in the first container 12 during mixing.

The first container 12 comprises a wall 22 defining a mixing chamber 24, an open lower end 26 and an open upper end 28. The first container 12 is preferably formed of a semi-rigid transparent or translucent material to enable the mixing process to be observed. The first container 12 is typically cylindrical shaped as shown. The mixing chamber 24 typically has a relatively small volume which allows a vacuum to be readily established and easily maintained. For example, the mixing chamber 24 can have a diameter of from about 1 in. to about 3 in.

A plunger 30 is disposed in the mixing chamber 24. As described below, the plunger 30 is moved axially in the mixing chamber 24 during dispensing of the mix from the mixing chamber 24.

A closure such as a removable cap 32 is attached to the wall 22 at the lower end 26. The cap 32 forms a gas-tight seal with the first container 12 during formation of a vacuum in the mixing chamber 24.

Referring to FIG. 3, the connector 16 is removably attached to the upper end 28 of the first container 12 by mating threads 34 formed on the connector 16 and the first container 12. A gasket 36 formed of a resilient material such as an elastomer is disposed to form a gas-tight seal between the first container 12 and the connector 16. The connector 16 defines an axial first passage 38 through which an agitator rod 40 of the agitator 18 extends from outside of the connector 16 to inside of the mixing chamber 24. A connector nut 42 is removably attached to the connector 16 by mating threads 44 formed on the connector 16 and the connector nut 42. The connector nut 42 includes an opening 46 therethrough for receiving the agitator rod 40. An O-ring 48 and a resilient gasket 50 form a gas-tight seal between the connector nut 42, the agitator rod 40 and the connector 16.

The agitator rod 40 preferably includes a longitudinal bore 52 extending along its length. A handle 53 is provided at an upper end of the agitator rod 40. A connector 54 such as a "Luer-Lok" connector is disposed in the bore 52 proximate to the handle 53. A poppet 56 is disposed at the lower end of the agitator rod 40.

The agitator 18 comprises at least one curved flexible paddle 58, and at least one curved, rigid blade 60, attached to the agitator rod 40. As shown in FIG. 4, the agitator 18 preferably comprises at least two flexible paddles 58. The flexible paddles 58 are fitted on a threaded end portion 62 of the agitator rod 40 and extend radially outward toward the wall 22. The agitator 18 preferably comprises at least four rigid blades 60 which also extend radially toward the wall 22. The rigid blades 60 can be approximately evenly angularly spaced from each other as shown in FIG. 6. The rigid blades 60 include threads 64 for removable attachment to the threaded portion 62 of the agitator rod 40.

The flexible paddles 58 are sufficiently flexible so that they are deflected by the mix during agitation, such that the flexible paddles 58 knead the mix. The flexible paddles 58 are preferably sized to contact the wall 22 of the mixing chamber 24 as shown in FIG. 5. Consequently, the flexible paddles 58 can effectively remove any of the mix adhered to the wall 22 such that the reaction material is well mixed. The flexible paddles 58 can be comprised of a suitable metallic or non-metallic material. For example, the material can be a plastic such as polyethylene or nylon, or a resilient metal such as a spring steel. The flexible paddles 58 typically have a thickness of from about 20 mil. to about 40 mil. The thickness of the flexible paddles 58 can be varied depending on the stiffness of the material from which they are formed. Generally, the stiffer the material, the thinner are the flexible paddles 58 to provide sufficient flexibility to knead the mix.

The rigid blades 60 are sufficiently rigid to maintain their shape and substantially not be deflected during agitation of the reaction materials, such that the rigid blades 60 can cut through the mix. The rigid blades 60 are preferably formed of a more rigid material than the flexible paddles 58. Accordingly, the thickness of the rigid blades 60 does not need to be greater than the thickness of the flexible paddles 58 to provide sufficient rigidity to substantially prevent deflection during agitation. The rigid blades 60 typically have a thickness of from about 20 mil. to about 40 mil. The rigid blades 60 can be formed of a suitable metallic or non-metallic material. The rigid blades 60 are preferably sized to contact the wall 22 of the mixing chamber 24 as shown in FIG. 6. Consequently, the rigid blades 60 can cut through the mix across the diameter of the mixing chamber 24.

Depending on the viscosity of the mix, the rigidity of the flexible paddles 58 and the rigid blades 60 can be varied such that the flexible paddles 58 are deflected and the rigid blades 60 are not deflected. Generally, as the viscosity of the mix increases, the rigidity of the both of flexible paddles 58 and the rigid blades 60 is increased.

The number of flexible paddles 58 and rigid blades 60 can be varied depending on the size of the first container 12. As the size of the first container 12 is increased, the number of flexible paddles 58 and rigid blades 60 is preferably increased to achieve effective agitation of the reaction materials. For example, the apparatus 10 can comprise two flexible paddles 58 and four rigid blades 60 as illustrated, or three flexible paddles 58 and six rigid blades 60 (not shown). The size of the flexible paddles 58 and the rigid blades 60 can also be increased as the size of the first container 12 is increased. The shape of the flexible paddles 58 and the rigid blades 60 can also be varied depending on the physical characteristics of the reaction materials. The rigid blades 60 and the flexible paddles 58 are preferably fabricated as separate components, so that different rigid blades 60 can be used in combination with flexible blades 58 of varying shape and flexibility, based on the physical characteristics of the reaction material to be mixed.

As shown in FIG. 3, the vacuum pump 20 can be removably attached to the connector 16. The vacuum pump 20 comprises a tubular portion 66 which is inserted into a second passage 68 in the connector 16. The second passage 68 is in flow communication with the mixing chamber 24 via a channel 70 between the agitator rod 40 and the connector 16.

A gas filter 72 is typically disposed inside the tubular portion 66 to prevent the escape of potentially hazardous gases from the mixing chamber 24 into the surrounding environment. The filter 72 is typically comprised of a small pore size fabric and an absorbent material such as activated charcoal for absorbing organic gas vapors. The filter medium can be selected depending on the materials that are mixed. There is only a small amount of air moved by applying the vacuum with the filter 72 positioned close to the mixing chamber 24 and with a high concentration of vapors at this location, so that the amount of charcoal needed in the filter 72 is small. The filter 72 prevents the harmful vapors that are evolved during the mixing of bone cement monomer from entering the environment.

A cap 74 is removably attached by mating threads 76 to the connector 16.

An O-ring 78 and a resilient gasket 80 form a gas-tight seal between the connector 16 and the vacuum pump 20.

The vacuum pump 20 includes a grip 82 and a handle 84 pivotally connected to the grip 82 for grasping by a user. The handle 84 is pivoted to draw gases from the mixing chamber 24 via the channel 70, the second passage 68 and an exhaust outlet 86 of the vacuum pump 20, to produce a desired vacuum level in the mixing chamber 24. A detachable vacuum indicator 88 shown in FIG. 2 can be provided to indicate the vacuum level in the mixing chamber 24.

The operation of the apparatus 10 is described in detail below with reference to the mixing of bone cement. The apparatus can be used to mix and dispense other multi-part reaction materials as well. The reaction materials can comprise, for example, two liquids, two pastes, or a powder and a liquid. The reaction material can be a cement as well as other types of materials such as adhesives. The reaction materials can have different viscosities and set times. The apparatus 10 is particularly advantageous for mixing viscous, short mix time reaction materials.

Bone cements comprise a liquid part and a powder part. The liquid part, typically a monomer such as methyl methacrylate, is conventionally supplied in a glass vial 90 or the like as shown in FIG. 1. The glass vial 90 can be placed into the second container 14 to store the monomer prior to mixing with the powder part. The powder part can be polymethyl methacrylate. The vial 90 can be placed into the second container 14 at the time of use, or alternately can be pre-packaged in the second container 14. The second container 14 is attached to the handle 53 of the agitator rod 40 at the connector 54. The agitator rod 40 can be moved up and down, as well as rotated, relative to the mixing chamber 24, while maintaining a vacuum in the mixing chamber 24. The agitator rod 40 is held in an axial fixed position by contact with the O-ring 48 and the gasket 50, and by contact between the flexible paddles 58 and the rigid blades 60 against the wall 22 of the first container 12.

The powder part 92 of the bone cement can be placed into the mixing chamber 24 either at the time of use, or as a pre-packaged item, by removing the cap 32 and the plunger 30 from the first container 12, and with the second container 14 detached from the agitator 18, the powder part 92 can be poured into the mixing chamber 24, passing through the open structure of the rigid blades 60 and the flexible paddles 58, and not entering the bore 52 of the agitator rod 40 due to the presence of the poppet valve 56. The plunger 30 is then placed back into the mixing chamber 24 at the lower end 26 followed by the attachment of the cap 32. The plunger 30 and the cap 32 each form an air-tight seal with the wall 22 of the first container 12 when a vacuum is formed in the mixing chamber 24. The filter 72 prevents the powder part 92 from escaping when the plunger 30 is in the mixing chamber 24; however, gas can pass through the filter 72 to enable the plunger 30 to be inserted into the mixing chamber 24.

Upon commencement of mixing, the cap 32 is in direct contact with the plunger 30 and the second container 14 is attached to the agitator rod 40. The cap 32 is placed on a solid surface such that the apparatus 10 is in an upright position, and the second container 14 is positioned as shown in FIG. 1. A retainer 94 disposed at the upper end of the second container 14 is then pushed downward, pushing the vial 90 against a breaker 96 in the second container 14 as shown in FIG. 7, so as to break the vial 90. Breaking the vial 90 allows the liquid part contained in the vial 90 to flow out through a filter screen 98, a connection portion 100 which engages the connector 54, and into the bore 52 of the agitator rod 40. Alternately, if there is a port valve (not shown) within the connector 54, the liquid part does not fill the agitator rod 40 at this time. A vent hole 102 is formed through the wall of the retainer 94 to allow air to enter the second container 14. This enables the liquid part to be easily pulled into the powder part 92. A one-way valve (not shown) can be provided in the vent hole 102 to allow air flow only in the direction into the second container 14. The bottom end 104 of the retainer 94 can be tapered as shown to approximately match the shape of the portion of the vial 90 that it contacts to enhance breaking of the vial 90. O-rings 106 can be provided on the retainer 94 to prevent vapors from escaping from the second container 14.

Following the breaking of the vial 90, the agitator rod 40 is pulled upward to above the powder part 92 in the mixing chamber 24. During the retraction of the agitator rod 40, some of the liquid in the bore 52 of the agitator rod 40 is pulled into the powder part 92. Once the flexible blades 58 and the rigid blades 60 are positioned above the powder part 92 in the mixing chamber 24, the handle 84 of the vacuum pump 20 can be slowly squeezed to gently pull the liquid down into the mixing chamber 24 and sprinkle it through the poppet valve 56 onto the powder part 92.

Alternately, if a port valve is located at the connector 54, the monomer may be added only to the top of the powder part 92, with liquid applied to the powder part 92, by means of the vacuum pump 20.

Alternately, the agitator rod 40 may be left in a fully down position in which the rigid blades 60 contact the plunger 30. The plunger 30 includes an indent 108 to provide sufficient space to enable the poppet valve 56 to downwardly open. The handle 84 of the vacuum pump 20 can be slowly squeezed to gently draw the monomer into the bottom of the mixing chamber 24, to allow the powder part to sink into the liquid part, thus adding the powder part to the liquid part.

Once the liquid part is completely emptied from the bore 52 of the agitator rod 40, the second container 14 is detached from the connector 54 and the vacuum indicator 88 is removed from the handle 84 of the vacuum pump 20 and placed on the connector 54 to seal the agitator rod 40 (FIG. 2). The handle 84 is squeezed until the vacuum indicator 88 indicates that the desired vacuum level is reached. The agitator rod 40 can then be pushed into the mixing chamber 24 so that the flexible paddles 58 and the rigid blades 60 contact the mix. The agitator rod 40 is turned clockwise and pressure is slowly applied to the handle 53 to immerse the flexible paddles 58 and the rigid blades 60 into the mix. It is preferable to perform numerous clockwise turns in combination with a slow descent of the agitator rod 40 until the rigid blades 60 reach the plunger 30. For improved mixing results and degassing, the cap 32 can be tapped on a solid surface every several rotations of the agitator rod 40. Upon reaching the plunger 30, the clockwise rotation of the agitator rod 40 is continued, while the flexible paddles 58 and the rigid blades 60 are preferably slowly raised within the mix until the flexible paddles 58 reach the upper end 28 of the mixing chamber 24. The mixing procedure is continued by slowly lowering the flexible paddles 58 and rigid blades 60 back into the mixing chamber 24 with clockwise rotations and then raising the agitator 18, until the prescribed mixing time for the reaction material is reached.

During mixing, the plunger 30 rises only a very small distance in the mixing chamber 24 under the influence of the vacuum because the cap 32 forms an airtight seal on the first container 12. As the pressure differential force tries to move the plunger 30 toward the upper end 28 of the mixing chamber 24, the small amount of air at atmospheric pressure located between the plunger 30 and the cap 32 is quickly reduced to a vacuum and the plunger 30 movement stops as a force balance is achieved.

During mixing, the rigid blades 60 cut the mix and contact the wall 22 of the first container 12 and scrape the powder part from the wall 22 and radially inward toward the center of the mixing chamber 24. The flexible paddles 58 simultaneously gently knead the mix and integrate the parts of the reaction material together. The combined action of the rigid blades 60 and the flexible paddles 58 forms channels through the mix, allowing entrapped air to escape to the vacuum. The rigid blades 60 and the flexible paddles 58 are sized and shaped so that they can reach substantially all of the open space in the mixing chamber 24 for enhanced agitation of the mix.

The slow, alternating in-and-out axial and rotational movement of the agitator 18 within the evacuated mixing chamber 24 can quickly produce a uniform, de-gassed material. The progress of the mix can be visually inspected through the wall 22 of the first container 24. Once the reaction material is mixed for the specified amount of time, or just before the end of the specified mix time as gas is being evolved from the reaction material, the handle 84 of the vacuum pump 20 can be pumped as needed to maintain the vacuum pressure in the mixing chamber 24 within the recommended range for the mixture.

All of the reaction by-product gases and removed air are evacuated through the filter 72 by the vacuum pump 20.

Once mixing is completed, the vacuum is maintained and the agitator rod 40 is raised so that the flexible paddles 58 are disposed at the neck 110 of the first container 12. In this position, the user firmly grasps the first container 12 with a hand placed preferably at about the location of the flexible paddles 58 and the rigid blades 60 in the mixing chamber 24. This firm grasp coupled with the semi-rigid construction of the first container 12 substantially prevents the agitator 18 from rotating. The agitator rod 40 is then rotated in the counter-clockwise direction while grasping the connector 16 and the vacuum pump 20 with the user's other hand. The counter-clockwise rotation unscrews the agitator rod 40 from the rigid blades 60 and the flexible paddles 58. Next, the first container 12 is unscrewed from the connector 16 by continuing the counter-clockwise rotation. Clockwise rotation during mixing maintains the gas-tight seals, while counter-clockwise rotation disassembles the apparatus (for right-hand thread connections). With the first container 12 detached from the connector 16, the cap 32 is then removed from the first container 12 and the first container 12 is placed in an extruding device such as a bone cement extrusion gun (not shown). A selected nozzle (not shown) for the extrusion procedure is attached via the threads 34 to the upper end 28 of the first container 12. The mix is then extruded into the surgical site.

Alternately, with the flexible paddles 58 positioned adjacent to the neck 110 and the connector 16, the cap 32 can be removed and the handle 84 of the vacuum pump 20 can be gently pumped to raise the plunger 30 upward under the action of the vacuum within the mixing chamber 24, the plunger 30 collecting the mixed material from the wall 22 as it moves. When the plunger 30 is positioned against the mix, the agitator rod 40 and the connector 16 can be unscrewed as described above, breaking the vacuum and preparing the mix for extrusion.

As the mix is extruded from the extruding device, which pushes on the plunger 30, the flexible paddles 58 collapse and fold back and downward into open spaces between the individual rigid blades 60. This folding action is the result of the shape of the flexible paddles 58 and their angular positioning on the agitator 40 with respect to the rigid blades 60, and allows substantially all of the mix to be extruded from the mixing chamber 24.

Thus, the apparatus 10 and method of mixing and dispensing multi-part reaction materials according to the present invention provides a number of important advantages. The apparatus 10 can rapidly introduce one part into another part in accordance with mixing schedules for the reaction materials. The mixing action avoids cavitation in the material mix and also reduces the entrapment of air. The apparatus 10 can efficiently agitate substantially the entire mixing chamber 24 at slow agitation speeds. The construction of the flexible paddles 58 and the rigid blades 60 exposes a large amount of surface area of the mix to vacuum, enabling trapped air and reaction gases to escape from even viscous mixes. The flexible paddles 58 and the rigid blades 60 move in unison to both cut the mix and scrape the wall 22 to well integrate the parts of the mix. In addition, the small mixing chamber 24 enables a vacuum to be quickly established and easily maintained.

The present invention can be provided as a kit. For example, when used to mix bone cement, the kit can include the powder part of the bone cement pre-packaged in the mixing chamber 24, and the liquid part pre-packaged in the second container 14, with the entire apparatus 10, including the attached vacuum pump 20 sterilized and ready for use.

The present invention has been described in considerable detail with reference to certain preferred embodiments thereof, however, other embodiments are possible. Therefore, the spirit and scope of the appended claims should not be limited to the description of the preferred embodiments contained herein.

What is claimed is:

1. An apparatus for mixing reaction materials under a vacuum, comprising:
    a) a container including a wall, an open first portion, an open second portion, and a mixing chamber sized to contain a reaction material during mixing;
    b) a closure at the second portion;
    c) an agitator for mixing the reaction material to form a mix, the agitator including:
        i) a plurality of rigid blades in the mixing chamber, the rigid blades being sufficiently rigid so as to be substantially non-deflected during mixing of the reaction material; and
        ii) a plurality of flexible paddles in the mixing chamber, the flexible paddles being sufficiently flexible so as to be deflected during mixing of the reaction material;
            wherein the rigid blades and the flexible paddles contact the wall of the container; and
    d) a channel in flow communication with the mixing chamber, gas being drawn from the mixing chamber through the channel to form a vacuum therein.

2. The apparatus of claim 1, further comprising an indicator to indicate the vacuum pressure in the mixing chamber.

3. An apparatus for mixing reaction materials under a vacuum, comprising:
    a) a first container including a wall, an open first portion, an open second portion and a mixing chamber sized to contain a reaction material during mixing;
    b) a closure at the second portion;
    c) an agitator for mixing the reaction material to form a mix, the agitator including:
        i) an agitator rod disposed in the mixing chamber and extending outwardly of the first container through the first portion;
        ii) at least one rigid blade in the mixing chamber, the rigid blade being sufficiently rigid so as to be substantially non-deflected during mixing of the reaction material; and
        iii) at least one flexible paddle in the mixing chamber, the flexible paddle being sufficiently flexible so as to be deflected during mixing of the reaction material;
            wherein at least one of the rigid blades and at least one of the flexible paddles contact the wall of the container; and
    d) a channel formed in the agitator rod and in flow communication with the mixing chamber, gas being drawn from the mixing chamber through the channel to form a vacuum therein.

4. The apparatus of claim 3, further comprising a connector and a vacuum pump attached to the second portion of the first container, the connector including a first passage through which the agitator rod extends, and a second passage through which gas is drawn from the mixing chamber by the vacuum pump to form the vacuum.

5. An apparatus for mixing reaction materials under a vacuum, comprising:
    a) a container including a wall, an open first portion, an open second portion and a mixing chamber sized to contain a reaction material during mixing;
    b) a closure at the second portion;
    c) an agitator for mixing the reaction material to form a mix, the agitator including:
        i) at least one rigid blade in the mixing chamber, the rigid blade being sufficiently rigid so as to be substantially non-deflected during mixing of the reaction material; and
        ii) at least one flexible paddle in the mixing chamber, the flexible paddle being sufficiently flexible so as to be deflected during mixing of the container;
            wherein at least one of the rigid blades and the flexible paddles contact the wall of the mixing chamber;
    d) a channel in flow communication with the mixing chamber, gas being drawn from the mixing chamber through the channel to form a vacuum therein; and
    e) a plunger sized to be inserted into the mixing chamber, the plunger being axially movable in the mixing chamber, to dispense the mix from the first container.

6. An apparatus for mixing reaction materials under a vacuum, comprising:
    a) a first container including a wall, an open first portion, an open second portion and a mixing chamber sized to contain a reaction material during mixing;
    b) a closure at the second portion;
    c) an agitator for mixing the reaction material to form a mix, the agitator including:
        i) at least one rigid blade in the mixing chamber, the rigid blade being sufficiently rigid so as to be substantially non-deflected during mixing of the reaction material; and
        ii) at least one flexible paddle in the mixing chamber, the flexible paddle being sufficiently flexible so as to be deflected during mixing of the reaction material;
            wherein at least one of the rigid blades and at least one of the flexible paddles contact the wall of the first container;
    d) a channel in flow communication with the mixing chamber, gas being drawn from the mixing chamber through the channel to form a vacuum therein; and e) a second container removably attached to the first container for containing a portion of the reaction material prior to introduction of the portion into the mixing chamber.

7. An apparatus for mixing reaction materials under a vacuum, comprising:
   a) a container including a wall, an open first end, an open second end, and a mixing chamber sized to contain a reaction material during mixing;
   b) a closure removably attached at the second end of the first container;
   c) an agitator for mixing the reaction material in the mixing chamber to form a mix, the agitator including:
      i) an agitator rod disposed in the mixing chamber and extending outwardly of the first container through the first end;
      ii) a plurality of rigid blades extending radially outward from the agitator rod and contacting the wall of the container, the rigid blades being sufficiently rigid so as to be substantially non-deflected during mixing of the reaction
      iii) a plurality of flexible paddles extending radially outward from the agitator rod and contacting the wall of the container, the flexible paddles being sufficiently flexible so as to be deflected during mixing of the reaction material,
         wherein the rigid blades and the flexible paddles being rotatable in the mixing chamber to form the mix;
   d) a bore through which a part of the reaction material is introduced into the mixing chamber; and
   e) a channel through which gas is drawn from the mixing chamber to form a vacuum therein.

8. The apparatus of claim 7, comprising a second container, a breakable container enclosing the part of the reaction material, and means for breaking the breakable container to release the part therefrom such that the part is drawn into the bore and introduced into the mixing chamber under the action of the vacuum.

9. The apparatus of claim 7, further comprising a connector and a vacuum pump, the connector being attached to the second end of the first container, the connector including a first passage through which the agitator rod movably extends, and a second passage through which gas is drawn from the mixing chamber by the vacuum pump.

10. The apparatus of claim 7, further comprising a plunger sized to be inserted into the mixing chamber, the plunger being axially movable in the mixing chamber to dispense the mix from the first container.

11. The apparatus of claim 7, further comprising an indicator to indicate the vacuum pressure in the mixing chamber.

12. The apparatus of claim 7, comprising at least two flexible paddles and at least four rigid blades.

13. A kit comprising:
   a) a first container including a wall, an open first end, an open second end and a mixing chamber;
   b) a closure at the second end;
   c) a second container removably connectable to the first container;
   d) an agitator for mixing a reaction material in the mixing chamber to form a mix, the agitator including:
      i) an agitator rod disposed in the mixing chamber and extending outwardly of the first container through the first end;
      ii) at least one rigid blade on the agitator rod, the rigid blade being disposed in the mixing chamber and contacting the wall of the first container, the rigid blade being sufficiently rigid so as to be substantially non-deflected during mixing of the reaction material; and
      iii) at least one flexible paddle on the agitator rod, the flexible paddle being disposed in the mixing chamber and contacting the wall of the first container, the flexible paddle being sufficiently flexible so as to be deflected during mixing of the reaction material;
   e) a bore in flow communication with the mixing chamber and the second container; and
   f) a vacuum pump removably connected to the first container for drawing gas from the mixing chamber to form a vacuum therein.

14. The kit of claim 13, comprising a plurality of rigid blades and a plurality of flexible paddles, each contacting the wall of the mixing chamber.

15. The kit of claim 13, further comprising a first part of a reaction material and a second part of the reaction material.

16. The kit of claim 15, wherein the first part comprises a liquid part of a bone cement mix, and the second part comprises a powder part of the bone cement mix.

17. The kit of claim 13, further comprising a connector removably attached to the second end of the first container, the connector including a first passage through which the agitator rod extends, and a second passage through which gas is drawn from the mixing chamber by the vacuum pump.

18. The kit of claim 13, further comprising a plunger sized to be inserted into the mixing chamber, the plunger being axially movable in the mixing chamber to dispense the mix from the first container.

19. The kit of claim 13, further comprising an indicator to indicate the vacuum pressure in the mixing chamber.

20. A method comprising:
   a) providing an apparatus as defined in claim 1, 2, 5, or 6:
   b) forming a vacuum in the mixing chamber;
   c) introducing a reaction material into the mixing chamber; and
   d) moving the rigid blades and flexible paddles in the mixing chamber to form a mix of the reaction material under the vacuum.

21. The method of claim 20, wherein the reaction material comprises a bone cement mix.

22. The method of claim 20, further comprising dispensing the mix from the mixing chamber.

23. The method of claim 20, wherein introducing comprises drawing a part of the reaction material into the mixing chamber under the vacuum.

* * * * *